United States Patent [19]

Masaki

[11] Patent Number: 4,689,039
[45] Date of Patent: Aug. 25, 1987

[54] ELECTROTHERAPEUTIC APPARATUS FOR IONTOPHORESIS

[75] Inventor: Kazumi Masaki, Osaka, Japan

[73] Assignee: Ken Hayashibara, Okayama, Japan

[21] Appl. No.: 881,117

[22] Filed: Jul. 1, 1986

[30] Foreign Application Priority Data

Jul. 19, 1985 [JP] Japan ................ 60-160900

[51] Int. Cl.⁴ ............................................. A61N 1/30
[52] U.S. Cl. ..................................... 604/20; 128/803
[58] Field of Search ......... 604/20; 128/419 R, 420 R, 128/421, 422, 790, 803

[56] References Cited

U.S. PATENT DOCUMENTS 4,340,047 7/1982 Tapper et al. ..................... 604/20

FOREIGN PATENT DOCUMENTS

| 0138347 | 4/1985 | European Pat. Off. ............... 604/20 |
| 2502015 | 9/1982 | France .................................. 604/20 |
| 124459  | 7/1983 | Japan . |
| 124458  | 7/1983 | Japan . |
| 124457  | 7/1983 | Japan . |
| 121963  | 7/1983 | Japan . |
| 1591817 | 6/1981 | United Kingdom . |
| 2113097 | 8/1983 | United Kingdom . |
| 2132892 | 7/1984 | United Kingdom ................... 604/20 |

OTHER PUBLICATIONS

*Fragrance Journal,* vol. 63, pp. 40–44, 1983.

*Primary Examiner*—Lee S. Cohen
*Attorney, Agent, or Firm*—Browdy and Neimark

[57] ABSTRACT

An electrotherapeutic apparatus is disclosed for iontophoretical removal of pigmentation, which comprises an electrode means (first electrode means) capable of bearing a mixture solution of kojic acid and a supporting electrolyte, and functioning as the active electrode in the iontophoresis; another electrode means (second electrode means) functioning as the dispersive electrode in the iontophoresis; and an oscillator means to generate a low-frequency voltage, said oscillator means having the output connected with the first- and second-electrode means in a manner that the potential at the first electrode means is lower than that at the second electrode means.

7 Claims, 8 Drawing Figures

ELECTROTHERAPEUTIC APPARATUS FOR IONTOPHORESIS

FIELD OF THE INVENTION

The present invention relates to an electrotherapeutic apparatus for iontophoresis, more particularly, to an electrotherapeutic apparatus to subcutaneously introduce kojic acid by iontophoresis.

BACKGROUND OF THE INVENTION

Melanism has been known as the major cause of freckles such as chloasma and melasma, and its therapy has been deemed very difficult.

*Fragrance Journal*, Vol. 63, pp. 40–44 (1983) reports that kojic acid (5-oxy-2-oxymethyl-γ-pyrone) is effective in suppressing and removing subcutaneous pigmentation, as well as proposes an external application of a cream composition containing kojic acid.

It is, however, very difficult to attain the expected therapeutic effect with such external application in a short period of time because of the limited amount of kojic acid that can be externally administered.

The present inventor investigated various means to remove pigmentation, and disclosed in Japan Patent Kokai Nos. 121963/83, 124457/83, 124458/83 and 124459/83 that subcutaneous absorption of a vitamin effective in removing pigmentation, specifically, vitamin C, is accelerated by iontophoresis.

My attempt to remove pigmentation by iontophoresis of kojic acid has proved unsatisfactory.

Further study shows that kojic acid does not form an effective amount of ion because its acid dissociation constants in aqueous solution, pKa, are relatively high, i.e. 7.90 and 8.03.

SUMMARY OF THE INVENTION

In view of the foregoing, the main object of the present invention is to provide means for to effect iontophoresis of kojic acid.

Another object of the present invention is to provide means for efficiently effecting the iontophoresis.

These and other objects as may be apparent hereinafter have been attained with the apparatus comprising an electrode means (first electrode means) capable of bearing a solution of kojic acid and a supporting electrolyte, and functioning as the active electrode in the iontophoresis; another electrode means (second electrode means) functioning as the dispersive electrode in the iontophoresis; and an oscillator means for generating a low-frequency voltage, said oscillator means having the output connected with the first- and second-electrode means in a manner that the potential at the first electrode means is lower than that at the second electrode means.

DESCRIPTION OF THE PREFERRED EMBODIMENTS

For a better understanding of the present invention as well as other objects and further features thereof, preferred embodiments of the invention will be explained with reference to the accompanying drawings in which.

Figure 1:
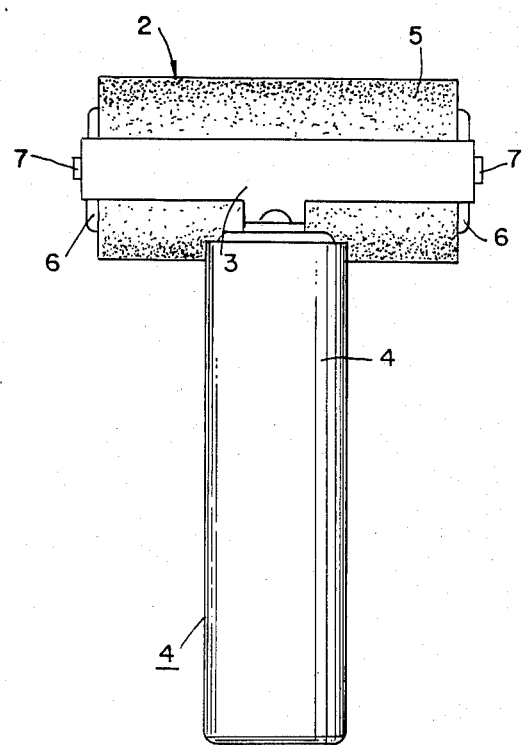
FIGS. 1 and 2 are the rear elevation- and side elevation-views of an electrotherapeutic apparatus according to the invention.

In the all accompanying drawings, reference numeral 1 designates the body of the electrotherapeutic apparatus; 2, moist-pad active electrode; 3, supporting means; 4, dispersive electrode; 5, cylindrical outer part made of a moisture retaining material; 6, electrode; and 7, projection.

Figure 2:
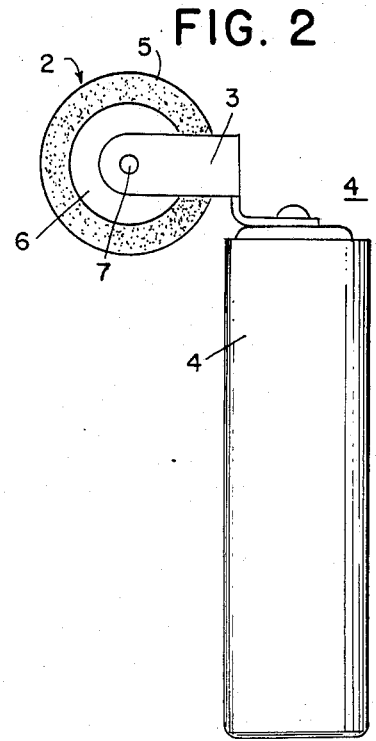
Figure 3:
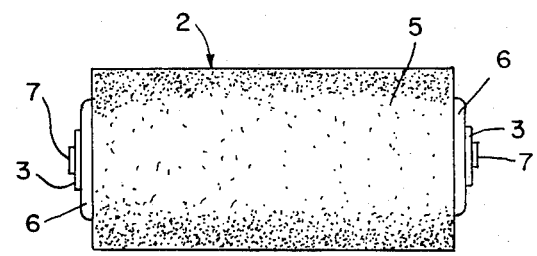
FIG. 3 is the front elevation-view of the moist-pad active electrode as shown in FIG. 1.

FIGS. 1 to 3 show an electrotherapeutic apparatus that can be favorably used for treating a relatively spread affected part.

In the embodiment as shown in FIGS. 1 and 2, roller-type moist-pad active electrode (2) is attached to the upper part of body (1) by supporting means (3), while dispersive electrode (4) is provided on the outside of body (1) wherein means for generating a negative low-frequency voltage and battery are placed.

As shown in FIG. 3, roller-type moist-pad active electrode (2) comprises cylindrical outer part (5) made of moisture-retentive material such as sponge, and cylindrical electrode (6). Cylindrical electrode (6) is inserted into cylindrical outer part (5), and the both ends of cylindrical outer part (5) are rollably attached to supporting means (3) by projection (7).

In use, for example, roller-type moist-pad active electrode (2) is soaked with a mixture solution that contains kojic acid and a supporting electrolyte, and then rolled over the affected part while applying a negative low-frequency voltage between roller-type moist-pad active electrode (2) and dispersive electrode (4).

Figure 4:
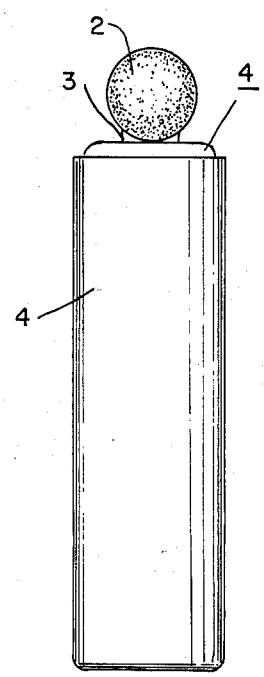
FIGS. 4 and 5 are the front elevation- and side elevation-views of an electrotherapeutic apparatus according to the invention.
Figure 5:
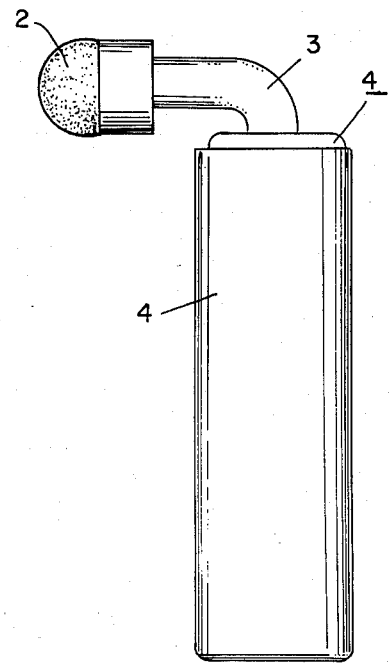

FIGS. 4 and 5 are illustrative of an electrotherapeutic apparatus that can be advantageously used for treating locally occurred freckles.

In this embodiment, in place of the roller-type moist-pad active electrode, projective small moist-pad active electrode (2) is attached to the upper part of body (1) with supporting means (3).

In use, for example, moist-pad active electrode (2) is soaked with a solution containing kojic acid and a supporting electrolyte similarly as in the case of the apparatus in FIGS. 1 and 2, a negative low-frequency voltage is then applied between moist-pad active electrode (2) and dispersive electrode (4) while keeping the end of the active electrode in contact with the affected part, to effect iontophoresis of kojic acid.

A long-term electrophoresis for a relatively spread affected part can be comfortably carried out with a plate-type moist-pad active electrode where a string or a rubber band is attached to the ends in a manner that the moist-pad active electrode satisfactorily conforms to the affected part.

As to the oscillator placed in body (1), any oscillator can be used as far as the kojic acid in moist-pad active electrode (2) can be iontophoretically introduced in the presence of a supporting electrolyte by connecting the output terminals of the oscillator with moist-pad active electrode (2) and dispersive electrode (4), in a manner that the potential at the active electrode is lower than that at the dispersive electrode, and energizing the output voltage between the electrodes.

The wording "low-frequency voltage" as referred in the invention is an alternating voltage with a frequency of 5,000 hertz or lower. In the alternating voltage, the negative component is larger in absolute magnitude than that of the positive component with respect to the zero potential line.

Figure 8:
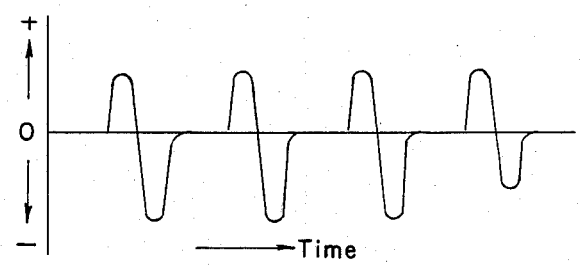
FIG. 8 is the waveform of a diphasic action potential.

Although conventional output waveforms such as square-, pulse-, sine-, triangular- and logarithmic-waves can be used in the invention, specifically suited is the low-frequency waveform obtained by superposing a diphasic action potential as shown in FIG. 8 on a square wave that should consist of a negative dc voltage or negative component and be lower in frequency than that of the diphasic action potential. Such low-frequency waveform will be called hereinafter "diphasic action potential". The pulse width and pulse interval are set respectively to 1/600-1/200 seconds and 1/200-1/20 seconds, and, when a square wave is used, its frequency is set to 0.5-5 hertz.

Figure 6:
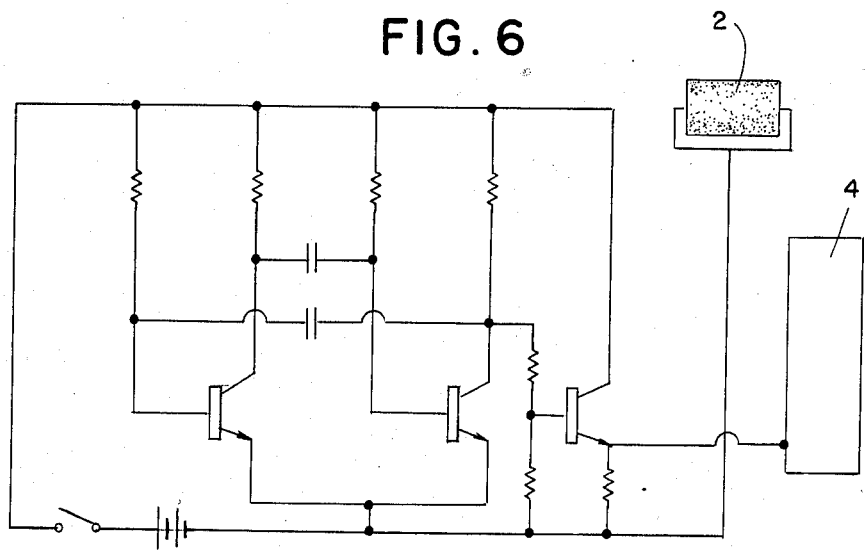
FIGS. 6 and 7 are the circuits that are used in the electrotherapeutic apparatus according to the invention.

FIG. 6 shows the circuit of an electrotherapeutic apparatus using a multivibrator wherein a negative square wave voltage is applied between moist-pad active electrode (2) and dispersive electrode (4).

Figure 7:
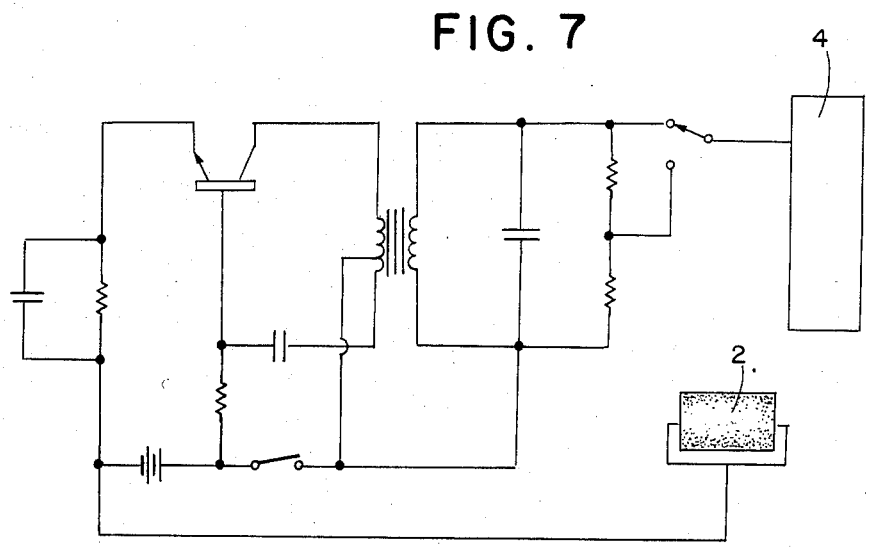

FIG. 7 shows the circuit of an electrotherapeutic apparatus using a blocking oscillator wherein a negative diphasic action potential is applied between moist-pad active electrode (2) and dispersive electrode (4).

The following illustrates the use of the apparatus according to the invention. Kojic acid is dissolved to give a concentration of 0.01-5 w/v %, specifically, 0.05-0.5 w/v %, in water or an alcoholic aqueous solution that contains a supporting electrolyte. Moist-pad active electrode (2) is soaked in the solution, and a low-frequency voltage of −1 to −50 volts, specifically −5 to −20 volts, is applied between moist-pad active electrode (2) and dispersive electrode (4) while holding dispersive electrode (4) provided on the outside of body of the apparatus (1) in a manner to keep moist-pad active electrode (2) in contact with the affected part. Thus, the iontophoresis of kojic acid is effected.

Alternatively, the iontophoresis can be effected by soaking moist-pad active electrode (2) in a solution containing a supporting electrolyte, applying a solution containing 1-3 w/v %, preferably, 5-20 w/v % of kojic acid, and operating the apparatus similarly as above.

The kojic acids usable in the invention are, in addition to intact kojic acid, derivatives of kojic acid, kojic acid salts such as sodium kojate and kojic acid complexes, as described in *Advances in Carbohydrate Chemistry*, Vol. 11, pp. 145-183 (1956), which have an activity of removing pigmentation but are non-toxic and free of side effect.

The supporting electrolytes usable in the invention are those which can be present in water, or saline, buffer or aqueous alcoholic solution thereof, and which accelerate the iontophoresis of kojic acid without causing undesirable chemical reaction when energized with a negative low-frequency voltage.

Examples of such supporting electrolytes are mineral acids, organic acids, amino acids and salts thereof. The specifically suited is vitamin C which, like kojic acid, accelerates iontophoresis of kojic acid as well as synergistically increases removal of pigmentation.

The amount of the supporting electrolyte is generally 0.1-100-folds, particularly, 2-20-folds against that of kojic acid, but varies with the type of supporting electrolyte.

The present inventor found that the use of the supporting electrolyte can be omitted by introducing ionic substituents, such as carboxyl group, into the moisture-retentive material used as the moist-pad active electrode (2) to impart ionic property to the electrode. Such moist-pad active electrode (2) is very convenient because it requires no supporting electrolyte.

The following experiments will explain the present apparatus.

EXPERIMENT 1

Acceleration of skin-permeability of kojic acid by iontophoresis

The openings of five test tubes were covered with freshly excised human skin specimens, and the test tubes were then filled with saline.

An electrotherapeutic apparatus as shown in FIG. 4 was equipped with a circuit as shown in FIG. 7, and the pulse width and pulse interval were set respectively to 1/300 seconds and 1/100 seconds. Kojic acid and vitamin C were dissolved in saline to give respective concentration of 0.1 w/v % and 0.3 w/v %, and projective small moist-pad active electrode (2) was then soaked in the resultant mixture solution.

Instantly on energizing 3 mA, −10 volts to moist-pad active electrode (2) while keeping it in contact with the skin, the kojic acid in the test tubes were determined by the method as reported in W. Hashida and T. Yamamoto, *Journal of Fermentation Technology*, Vol. 30, pp. 354-358 (1952) utilizing the coloration reaction of ferric chloride.

Simultaneously tested were a system with diphasic action potential but with no addition of vitamin C (Control 1), and a system wherein vitamin C and diphasic action potential were omitted (Control 2).

The amounts of kojic acid that passed through the skin were 450 with the present invention and 150 in Control 1 when evaluated with the amount in Control 2 as 100.

These data confirmed that the iontophoresis in the presence of the supporting electrolyte extremely accelerated skin permeability of kojic acid.

EXPERIMENT 2

Clinical Tests

Based on the data of Experiment 1, the following clinical tests were conducted.

The output of an oscillator as shown in FIG. 7 was set to a pulse width of 1/300 seconds and a pulse interval of 1/50 seconds, and then equipped in an electrotherapeutic apparatus as shown in FIGS. 1 and 4.

Clinical tests were conducted with 200 chloasma patients at 6 hospitals.

In the therapy, kojic acid and vitamin C were dissolved in saline to give respective concentration of 0.1 w/v % and 0.5 w/v %, and moist-pad active electrode (2) was then soaked in the resultant mixture solution, after which the negative diphasic action potential was energized between moist-pad active electrode (2) and dispersive electrode (4) to effect iontophoresis while keeping the end of the active electrode in contact with the affected part.

Simultaneously tested were a system with diphasic action potential but with no addition of vitamin C (Control 1), a system with no addition of kojic acid but with diphasic action potential (Control 2), and a system wherein vitamin C and diphasic action potential were omitted and wherein the kojic acid solution was applied over the affected part (Control 3).

The therapy was conducted by either doctor or physiotherapist and, with one dose, the diphasic action potential, −5 to −20 volts, was administered for a duration of 5 to 30 minutes. This was repeated for one month while monitoring the patients' affected parts.

After a lapse of one month, the doctor observed the patients' affected parts, and interviewed the patients for the efficacy. The data were grouped into "very efficacious", "slightly efficacious", "inefficacious", and "worsened". The cure ratio was evaluated by calculating the percentage of "very efficacious" plus "slightly efficacious" to the 50 patients who participated the particular system.

The results were as shown in Table I.

TABLE I

|  | (number of the subjects) | | | |
|---|---|---|---|---|
|  | Present invention | Control 1 | Control 2 | Control 3 |
| Very efficacious | 38 | 4 | 1 | 2 |
| Slightly efficacious | 3 | 15 | 5 | 9 |
| Inefficacious | 6 | 26 | 42 | 35 |
| Worsened | 3 | 5 | 2 | 4 |
| Cure ratio (%) | 82 | 38 | 12 | 22 |

As apparent from these results, the iontophoresis using the supporting electrolyte is synergistically about 2 and 3.7-fold efficacious than with Controls 1 and 3.

Further, in Controls, specifically in Control 3, side effects such as leukopathy have been noted with some patients, while in the system according to the invention the therapy could be comfortably carried out.

Based on these results, additional clinical tests were conducted at 9 hospitals; most of the patients suffered from either of the pigmentation of Riel's melanosis, bilin spots and ephelis. The efficacy was showed higher than 80% over a short period of time.

As described above, pigmentation can be efficiently removed by effecting iontophoresis of kojic acid in the presence of a suitable supporting electrolyte such as vitamin C according to the invention. The efficacy attained by the use of present invention is synergistically higher than that attained either by application of kojic acid or iontophoresis without a supporting electrolyte. By the practice of the present invention, removal of pigmentation caused by chloasma or Riel's melanosis, which has been deemed very difficult, can be efficiently and comfortably attained in a short period of time.

While the present invention has been particularly shown and described with reference to preferred embodiments thereof, it will be understood by those skilled in the art that the foregoing and other changes in form and details can be made therein without departing from the spirit and scope of the invention.

I claim:

1. An electrotherapeutic apparatus for iontophoresis, comprising:
   (a) first electrode means bearing a solution of kojic acid and a supporting electrolyte, and functioning as the active electrode in the iontophoresis;
   (b) second electrode means functioning as the dispersive electrode in the iontophoresis; and
   (c) an oscillator means for generating a low-frequency voltage, said oscillator means having outputs connected with the first and second electrode means in a manner that the potential at the first electrode means is lower than that at the second electrode means.

2. The apparatus of claim 1, wherein the supporting electrolyte is vitamin C.

3. The apparatus of claim 1, wherein the concentration of kojic acid is in the range of 0.01 to 5 w/v %.

4. The apparatus of claim 1, wherein said oscillator means is a blocking oscillator.

5. The apparatus of claim 1, wherein said low-frequency voltage is a train of diphasic pulses.

6. The apparatus of claim 1, wherein the first electrode means is a moist-pad active electrode.

7. The apparatus of claim 1, wherein the first electrode means is composed of ion exchange material.

* * * * *